United States Patent [19]

Saucy

[11] 4,153,615

[45] May 8, 1979

[54] METHOD OF PRODUCING COLORING AGENTS

[75] Inventor: Gabriel Saucy, Essex Fells, N.J.

[73] Assignee: Hoffmann-La Roche Inc., Nutley, N.J.

[21] Appl. No.: 890,173

[22] Filed: Mar. 27, 1978

[51] Int. Cl.² .................................. C07D 317/10
[52] U.S. Cl. .................. 260/340.9 R; 260/586 R; 260/606.5 F; 560/231; 568/828
[58] Field of Search ................................ 260/340.9 R

[56] References Cited

U.S. PATENT DOCUMENTS

| | | | |
|---|---|---|---|
| 3,732,214 | 5/1973 | Surmatis et al. | 260/340.9 R X |
| 3,875,241 | 4/1975 | Corbier et al. | 260/340.9 R X |
| 3,953,516 | 4/1976 | Corbier et al. | 260/340.9 X |

*Primary Examiner*—Ethel G. Love
*Attorney, Agent, or Firm*—Jon S. Saxe; Bernard S. Leon; William H. Epstein

[57] ABSTRACT

A method of stereo-specifically synthesizing Zeaxanthin and alloxanthin, natural food coloring agents from 2,6,6-trimethyl-1,4-cyclohexanedione including intermediates in this synthesis.

8 Claims, No Drawings

METHOD OF PRODUCING COLORING AGENTS

SUMMARY OF INVENTION

In accordance with this invention, a new stereospecific synthesis directed to natural food coloring agents of the formula

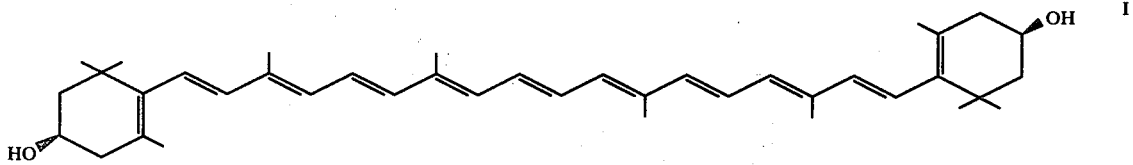

and

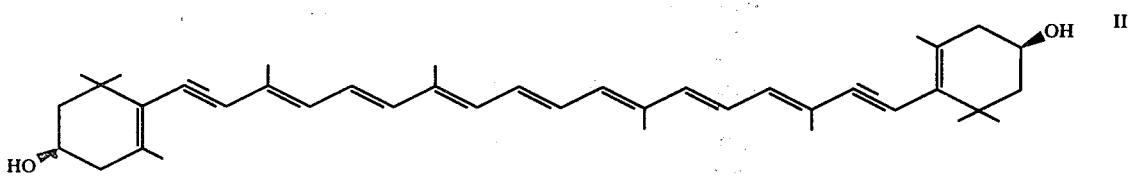

from a compound of the formula

In accordance with one aspect of the process, the compound of formula III is converted stereospecifically to the intermediate

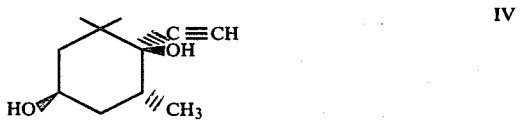

The compound of formula IV, due to its stereoconfiguration, is a known intermediate for Zeaxanthin (compound of formula I). It is through the stereoconfiguration of the compound of formula IV and through the process of this invention that allows one to prepare the natural Zeaxanthin while the hydroxy substituents on each of the cyclohexene rings having the beta configuration.

DETAILED DESCRIPTION

In the formula presented herein, the various substituents on the cyclic moiety are joined in the cyclic nucleus by one of two notations: a solid bar (◂) indicating a substituent which is in the beta-orientation (i.e. above the plane of the paper) and a broken line ( ⫶ ) indicating a substituent which is in the alpha-orientation (below the plane of the paper).

The term "lower alkyl" designates saturated aliphatic hydrocarbon groups containing from 1 to 7 carbon atoms such as methyl, ethyl, n-propyl, isopropyl, isobutyl, etc. The term halogen includes all four halogens, i.e. chlorine, fluorine, iodine and bromine. Also, the term alkali metal includes lithium, sodium, potassium, rubidium and cesium.

The term lower alkanoyl designates a lower alkanoyl substituent containing from 2 to 7 carbon atoms such as acetyl and butyryl. As used herein, the term aryl includes mono-nuclear aryl groups such as phenyl which can be unsubstituted or substituted in one or more positions with a lower alkyl group as well as polynuclear aryl groups such as naphthyl, anthryl, phenanthryl and azalyl which may be unsubstituted or substituted with one or more of the aforementioned substituents. The term aroyl designates aroyl wherein aryl is defined as above. The preferred aroyl group is benzoyl.

In accordance with this invention, the compound of formula III is converted into the compound of formula IV via the following intermediates:

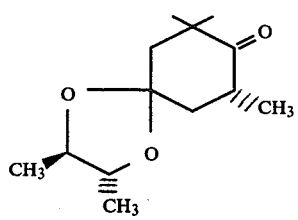

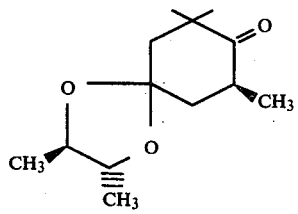

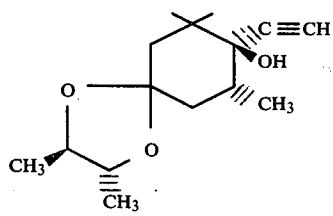

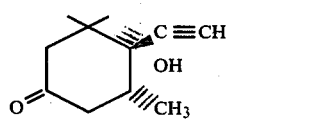

In carrying out the conversion of a compound of formula III to a compound of formula V, the compound of formula III is reacted with D(−)-butyleneglycol having the formula

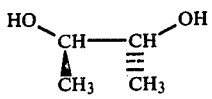

The reaction of the compound of formula III with the compound of formula X can be carried out utilizing any conventional method for ketalizing a ketone with an alkylene glycol. Among the preferred methods is to react the compound of formula III with the compound of formula X in the presence of an acid catalyst. In carrying out this reaction, any conventional acid catalyst can be utilized. Among the preferred acid catalysts are the strong inorganic acids such as sulfuric acid and the strong organic acids such as p-toluene sulfonic acid. Generally, this reaction is carried out in an inert organic solvent. Any conventional inert organic solvent can be utilized in carrying out this reaction. Among the preferred solvent are the aromatic hydrocarbon solvents such as benzene, toluene, etc. Generally, this reaction is carried out at the reflux temperature of the reaction medium with azeotropic removal of water. Any conventional device for azeotropic removal of water can be utilized in this reaction e.g. a Dean Stark trap.

In accordance with this invention, the reaction of a compound of formula III with a compound of formula X produces the compound of formula V in a mixture with the compound of formula V-a. The compound of formula V is easily obtained from this mixture since it is less soluble than the compound of formula V-a in inert organic solvents and readily crystallizes. Therefore, upon reaction of the compound of formula III with the compound of formula X in an inert organic solvent, the compound of formula V can be crystallized leave the compound of formula V-a in the mother liquor. The mother liquor can also contain some compound of formula V.

The compound of formula V-a in the mother liquor can be converted to the compound of formula V. If desired, the compound of formula V-a can be isolated from the mother liquor in which it was formed by conventional means. However, for the sake of economy, it is best to treat the mother liquor without isolating the compound of formula V-a. The compound of formula V-a or mixtures of the compound of formula V-a with the compound of formula V such as found in the mother liquor can be converted into the compound of formula V by equilibration. Any conventional method of equilibration can be utilized to convert the compound V-a or mixtures thereof with the compound of formula V to the compound of formula V in crystalline form. Among the preferred methods is to treat the compound of formula V-a or mixtures thereof with the compound of formula V with a strong base in the presence of an inert organic solvent medium. Any conventional strong base can be utilized. Among the preferred bases are the alkali metal and alkaline earth metal hydroxides such as sodium hydroxide, calcium hydroxide, potassium hydroxide, etc. Additionally the strong base can be an alkali metal carbonate or an alkaline earth metal carbonate such as sodium carbonate, potassium carbonate, etc. On the other hand, a strong base can be an alkali metal lower alkoxide such as sodium methoxide. Generally the equilibration reaction is carried out in an inert organic solvent. Any conventional inert organic solvent can be utilized. Among the preferred inert organic solvents are the ether solvents such as diethyl ether, dioxane, lower alkanols such as methanol, ethanol, etc., aliphatic hydrocarbon solvents such as hexane, etc. If desired, water can be present in the reaction medium. In carrying out the equilibration, temperature and pressure are not critical and this reaction can be carried out at room temperature and atmospheric pressure. On the other hand, temperatures ranging from 10° C. to 150° C. can be utilized.

The compound of formula V is converted to the compound of formula V1 by reacting the compound of formula V with a compound of the formula $$C\equiv C-Mg X \qquad XI$$

wherein X is a halide. In carrying out this reaction, any of the conditions conventional in Grignard synthesis can be utilized. On the other hand, the compound of formula V can be converted to the compound of formula VI by reacting the compound of formula V with an alkali metal acetylide such as sodium or lithium acetylide. Any of the conditions conventional in reacting a ketone with acetylide to form an addition product can be utilized in accordance with this invention. Generally, this reaction is carried out in liquid ammonia.

The compound of formula VI is converted to the compound of formula VII by acid hydrolysis. Any conventional method of hydrolyzing a ketal derivative to a ketone can be utilized. Among the preferred methods for carrying out this reaction is by treating with an organic acid such as acetic acid at temperatures of from 50°–100° C.

The compound of formula VII is converted to the compound of formula IV by reduction with a lower alkoxy alkali metal aluminum hydride. Any conventional lower alkoxy alkali metal aluminum hydride reducing agents can be utilized for this selective reduction. Among the preferred lower alkoxy alkali metal aluminum hydrides are lithium (tri-tertiary butoxy-aluminum hydride and sodium bis-(2-methoxyethoxy) aluminum hydride. In carrying out this reaction, any of the conventional conditions utilized in reduction with a hydride reducing agent can be utilized. In carrying out this reduction, it is generally preferred to utilize an inert organic solvent such as ethylene chloride, benzene and toluene. In fact, any conventional inert organic solvent can be utilized. In carrying out this reduction, temperature and pressure are not critical and this reaction can be carried out at room temperature and atmospheric pressure. On the other hand, temperatures of from 10° C. to 100° C. can be utilized.

In accordance with another embodiment, the compound of formula V is converted to alloxanthin (the compound of formula II) via the following intermediates:

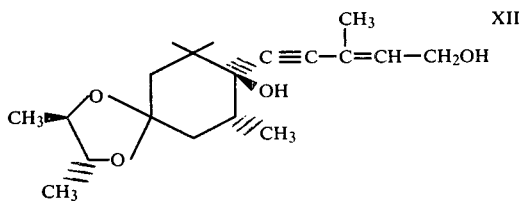

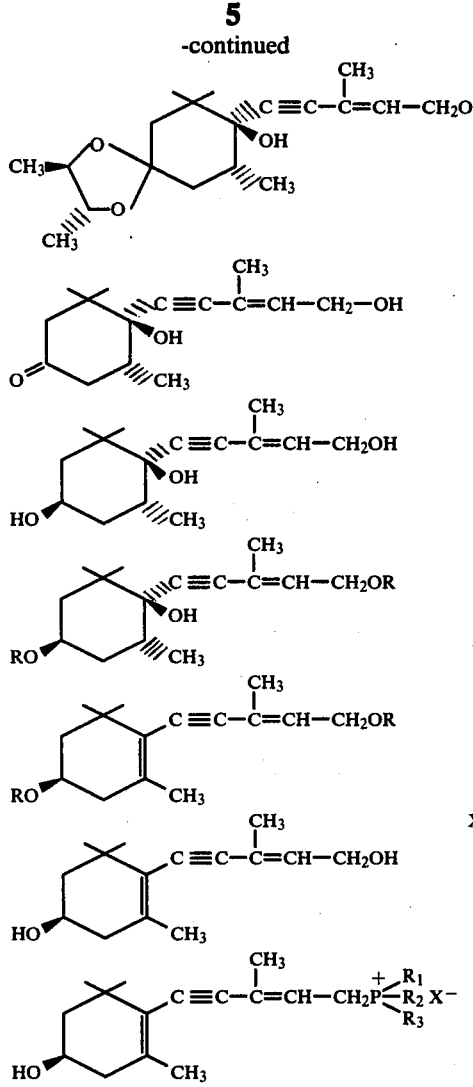

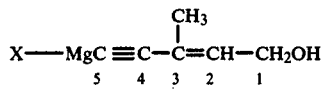

wherein R₁ is lower alkanoyloxy, or aroyloxy; and R₁, R₂ and R₃ are lower alkyl or aryl; and X is as above.

In converting the compound of formula V to the compound of formula XII, the compound of formula V is reacted with a organo metallic halide of the formula $$X\text{—}MgC\equiv C-\underset{\underset{3}{|}}{\underset{CH_3}{C}}=CH-CH_2OH \quad XX$$
$$\phantom{X\text{—}MgC\equiv}5\phantom{-}4\phantom{=}3\phantom{=CH}2\phantom{-CH_2O}1$$

wherein X is as above.

In the compound of formula XX above, the substituents across the 2,3 double bond can be in the trans or cis configuration or mixture thereof. The particular geometric configuration across the double bond could be carried in accordance with the process of this invention throughout all of the subsequent intermediates to the corresponding position on the final products.

The reaction of the compound of formula XX with a compound of the formula V is carried out utilizing a conventional Grignard synthesis. This reaction is carried out in the same manner as described in connection with the reaction of a compound of the formula V with a compound of the formula XI to produce a compound of the formula VI. In this reaction, the compound of the formula XII is in a mixture with a compound of the formula:

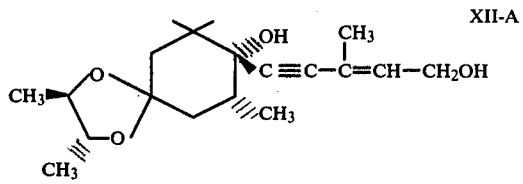

A mixture of the compound of formula XII and the compound of formula XII-A can be separated by conventional means. Among the preferred methods separating the compound of formula XII with the compound of formula XII-A is to produce an ester of the compound of the formula XII, i.e. a compound of the formula XIII. Any conventional method of esterifying a hydroxy group with a reactive derivative of a lower alkanoic or aroic acid can be utilized. The preferred ester for use in separation is benzoic acid Hence, the compound of formula XII is converted to the compound of formula XIII by esterification through the reaction with a reactive derivative of a lower alkanoic or aroic acid such as an acid halide. The esters can be easily separated by a conventional means such as chromatography. After separation the compound of formula XIII is hydrolyzed with a base to produce a compound of formula XII in pure form. Any conventional method of basis hydrolysis to convert an ester into an alcohol can be utilized to convert the compound of formula XIII to a compound of the formula XII.

The compound of formula XII is converted to the compound of formula XIV by ketal cleavage such as described in connection with the conversion of a compound of the formula VI to a compound of the formula VII. The compound of the formula XIV is reduced to a compound of the formula XV by treatment with an alkali metal lower alkoxy aluminum hydride. This reaction is carried out in the same manner as described in connection with the conversion of a compound of formula VII to a compound of formula IV. The compound of formula XV is converted to the compound of formula XVI by esterification with a reactive derivative of a lower alkanoic acid or aroic acid. Any conventional method of esterifying an alcohol with a organic acid can be utilized to convert the compound of formula XV to the compound of formula XVI.

The compound of formula XVI is converted to the compound of formula XVII by treatment with a dehydrating agent. Any conventional dehydrating agent can be utilized to effect this conversion. Among the preferred dehydrating agents are the acid dehydrating agents such as phosphorus oxychloride, sulfuric acid, etc. Any conventional acid dehydrating agent can be utilized to carry out this reaction. In carrying out this reaction, temperatures of from 60° C. to 120° C. are generally utilized, with the reflux temperature being generally preferred. In carrying out this reaction, an inert organic solvent medium can be utilized. Any conventional inert organic solvent can be utilized as the reaction medium.

The compound of formula XVIII is converted to the compound of formula XIX by reaction with a hydrohalic salt of the formula

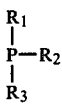

wherein $R_1$, $R_2$ and $R_3$ are as above. The compound of formula XVIII is reacted with a hydrohalide salt of the compound of formula XXI in the presence of an inert organic solvent. Among the hydrohalic acid salts, triphenylphosphine hydrobromide is preferred. In carrying out this reaction, any conventional inert organic solvent can be utilized as the reaction medium. Among the preferred solvents are included the halogenated hydrocarbon solvents such as dichloromethane, methylenechloride, etc. In carrying out this reaction, temperature and pressure are not critical and this reaction can be carried out at room temperature and atmospheric pressure. If desired, higher or lower temperatures can be utilized.

The compound of formula I is formed from the compound of formula XIX by reacting the compound of formula XIX with a compound of the formula

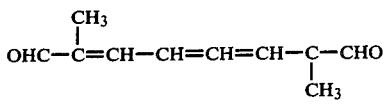

via a Wittig reaction.

This reaction is carried out utilizing conditions that are conventional in Wittig-type reactions. In this reaction, two moles of the compound of formula XIX are reacted per mole of the compound of formula XXII.

The invention will be more fully understood from the specific examples which follow. These examples are intended to illustrate the invention and are not to be construed as limitative thereof.

EXAMPLE 1

2(R),3(R),7,7,9(R)-pentmethyl-1,4-dioxaspiro-[4.5]-decan-8-one 100 g of 2,2,6-trimethyl-1,4-cyclohexanedione 77 g of (−)-2,3-butandiol, 2 g of p-toluenesulfonic acid and 1000 ml of benzene were introduced in a reaction flask mounted with a water trap and refluxed for four hours. The reaction mixture was cooled at room temperature and then it was poured in 250 ml of a saturated aqueous sodium bicarbonate solution. The organic phase was separated, washed with brine, dried on magnesium sulfate and the solvent evaporated in vacuo.

152 g of the crude material was diluted in a mixture of 100 ml of carbon tetrachloride and hexane (1:1 parts by volume) and allowed to crystallize slowly first at room temperature then in a refrigerator at −15° C. for 2 weeks.

21.5 g of 2(R),3(R),7,7,9(R)-pentamethyl-1,4-dioxaspiro-[4,5]-decan-8-one was obtained from the mother liquor in the form of large crystals and dried under vacuo overnight. A recrystallized sample gave 2(R),3(R),7,7,9(R)-pentamethyl-1,4-dioxaspiro-[4.5]-decan-8-one: m.p. 71°–72° C., from CCl₄/hexane.

EXAMPLE 2

127.4 g of the mother liquor of example 1, which showed on a column (carbowax) a mixture of 2(R),3(R),7,7,9(R)-pentamethyl-1,4-dioxaspiro-[4.5]-decan-8-one and 2(R),3(R),7,7,9(S)-pentamethyl-1,4-dioxaspiro-[4.5]-decan-8-one in ratio 1:1.5 parts by weight was dissolved in 500 ml of a 5% by weight aqueous solution of sodium hydroxide in 95% by volume aqueous methanol and heated at 60° C. for two days. Most of the solvent (ca 300ml) was evaporated in vacuo. The residue was dissolved in ether, washed five times with water, dried on magnesium sulfate and the solvents evaporated at reduced pressure. From 105.7 g of crude material was crystallized 10.2 g of 2(R),3(R),7,7,9(R)-pentamethyl-1,4-dioxaspiro-[4.5]-decan-8-one.

An additional 11.3 g of 2(R),3(R),7,7,9(R)-pentamethyl-1,4-dioxaspiro-[4.5]-decan-8-one was obtained from 81.1 g crude material after treatment of the mother liquor (86.4 g) with 5% by volume methanolic sodium hydroxide. Total yield 29.2% of the theory. The last mother liquor (68.4 g) contained still more than 75% of the isomeric mixture of 2(R),3(R),7,7,9(R)-pentamethyl-1,4-dioxaspiro-[4.5]-decan-8-one and 2(R),3(R),7,7,9(S)-pentamethyl-1,4-dioxaspiro-[4.5]-decan-8-one

EXAMPLE 3

8(S)-Ethynyl-2(R),3(R),7,7,9(R)-pentamethyl-1,4-dioxaspiro[4,5]decan-8-ol

A stream of acetylene gas was introduced through a gas inlet tube in a 500 ml three-necked flask containing a Grignard solution prepared from 1.56 g of magnesium turnings 8.16 g of ethylbromide in 100 ml of dried tetrahydrofuran at 10° to 15° C (ice-water bath) for 2 hours and under argon. To the reaction mixture was added an additional 80 ml of tetrahydrofuran to avoid the precipitation of the Grignard salt.

6.78 g of 2(R),3(R),7,7,9(R)-pentamethyl-1,4-dioxaspiro-[4,5]-decan-8-one in 70 ml of tetrahydrofuran was added dropwise at 10° C. and then the resulting mixture was stirred under argon at room temperature for 17 hours. The reaction mixture was poured into 100 ml of a saturated aqueous ammonium chloride solution and the organic phase was separated. It was combined with two 100 ml ether extracts of the aqueous phase, washed with brine, dried over magnesium sulfate and the solvents evaporated in vacuo to give 7.8 g (ca. 100% yield) of crude 8(S)-ethynyl-2(R),3(R),7,7,9(R)-pentamethyl-1,4-dioxaspiro-[4,5]-decan-8-ol. Crystallization from isopropylether a afforded 6.3 g (83.2%) of 8(S)-ethynyl-2(R),3(R),7,7,9(R)-pentamethyl-1,4-dioxaspiro-[4,5]-decan-8-ol (m.p. 79–83° C; GC-analysis:>98% purity). An analytical sample was obtained by recrystallization from isopropylether: m.p. 83°–85° C.

EXAMPLE 4

4(S),5(R)-4-Ethynyl-4-hydroxy-3,3,5-trimethylcyclohexan-1-one 5 g of 8(S)-ethynyl-2(R),3(R),7,7,9(R)-pentamethyl-1,4-dioxaspiro[4,5]decan-8-ol (m.p.79–83° C.) was dissolved in 30 ml of an 80% by volume aqueous acetic acid solution and stirred at 70° C. for 3 hours. The solution was saturated with sodium chloride and extracted several times with methylene chloride. The organic extracts were combined, washed with brine, aqueous sodium bicarbonate solution, brine and then dried on magnesium sulfate.

3.6 g (ca 100%) of the crude compound 4(S),5(R)-4-ethynyl-4-hydroxy-3,3,5-trimethylcyclohexan-1-one was obtained (97% by GC-analysis), after removal of the solvent in vacuo. Crystallization from ether yielded.

3.09 g (85.8%) of material, m.p.140°–143° C. An analytical sample was obtained after recrystallization from ether-hexane: m.p.141°–143° C.

EXAMPLE 5

1(S),4(R)-1-Ethynyl-2,2,6-trimethyl-1,4-cyclohexanedid 1.2 g of the crystalline 4(S),5(R)-4-ethynyl-4-hydroxy-3,3,5-trimethylcyclohexan-1-one dissolved in 20 ml of dried tetrahydrofuran was added slowly to a suspension of 3.2 g of lithium tri-tert-butoxy aluminum hydride in 40 ml of dried tetrahydrofuran at 0° to 5° C. The mixture was stirred first at 5° C. for 30 minutes, then at room temperature for 17 hours and finally was gently refluxed for 1 hour.

16 ml of a 5% by volume aqueous acetic acid solution was added carefully at 0° C. under stirring (pH ca. 6). The mixture was saturated with sodium chloride and extracted several times with ether. The organic phase was dried over magnesium sulfate and the solvents removed in vacuo to yield 1.53 g of crude material. Crystallization from ether-hexane afforded 0.900 g (74.1%) of compound 1(S),4(R),6(R)-1-ethynyl-2,2,6-trimethyl-1,4-cyclohexanediol (m.p.150°–152° C.; GC-analysis:>98% pure). The recrystallization of this material yielded 0.850 g of pure product, m.p.150°–152° C.; GC: no impurity; $[\alpha]25D = -24.93$ (1% in dioxane.

EXAMPLE 6

To 0.540g of 4(S),5(R)-4-ethynyl-4-hydroxy-3,3,5-trimethylcyclohexan-1-one in benzene was dropped 2.1 g of bis(2-methoxyethoxy)-aluminum hydride (70% in benzene) to give 0.518 g of the desired isomer 1(S),4(R),6(R)-1-ethynyl-2,2,6-trimethyl-1,4-cyclohexanediol based on GC-analysis). The conditions for the reduction were the same as in Example 5.

EXAMPLE 7

1(R),4(S),5(R)-4-ethynyl-4-hydroxy-3,3,5-trimethyl-cyclohexyl acetate 0.140g of the pure 1(S),4(R),6(R)-1-ethynyl-2,2,6-trimethyl-1,4-cyclohexanediol was dissolved in 2 ml of a mixture of acetic anhydride-pyridine (1:1 parts by volume) and stirred at room temperature under argon for 17 hours. The resulting light yellow solution was concentrated to dryness at 70° C., 12 mm Hg to afford 156 g of crude 1(R),4(S),5(R)-4-ethynyl-4-hydroxy-3,3,5-trimethyl-cyclohexyl-acetate, m.p.69.5°–72.5° C.;$[60]_D^{25} = -22.85$(1% in dioxane). Recrystallization from ether-hexane gave 0.129g of pure 1(R),4(S),5(R)-4-ethynyl-4-hydroxy-3,3,5-trimethyl-cyclohexyl acetate.

EXAMPLE 8

8(S)-E-(5-Hydroxy-3-methylpent-3-en-1-yn-yl)-2(R),3(R),7,7,9(R)-pentamethyl-1,4-dioxaspiro[4,5]decan-8-ol To a Grignard solution of 1.55g of magnesium activated with iodine, 7.00g of ethylbromide in 100 ml dried tetrahydropyran was added dropwise to 2.6g of trans-pentol in 25 ml dried tetrahydrofuran at 10° C. to 15° C. (cold water bath). The reaction mixture was stirred 30 minutes at room temperature; then it was heated at 50° C. for 20 minutes. The water bath was removed and 5.5g of 2(R),3(R),7,7,9(R)-pentamethyl-1,4-dioxaspiro-[4.5]-decan-8-one dissolved in 25 ml dried tetrahydrofuran was added dropwise at room temperature. The new reaction mixture was poured into 50 ml of a saturated ammonium chloride solution and the reaction flask was rinsed with ether. The etheral solution was washed twice with brine, dried on magnesium sulfate and evaporated in vacuo to give 9.1g of material. This crude product was chromatographed on (364 grams) Aluminum oxide. Ether-hexane 4:1 (parts by volume) eluted a mixture 5.67g (72% of the theory) of 8(S)-E-(5-hydroxy-3-methylpent-3-en-1-yn-yl)-2(R)-3(R),7,7,9(R)-pentamethyl-1,4-dioxaspira[4.5]decan-8-ol and 8(R)-E-(5-hydroxy-3-methylpent-3-en 1-yn-yl)-2(R),3(R),7,7,9(R)-pentamethyl-1,4-dioxoaspira[4.5]decan-8-ol.

EXAMPLE 9

6.1g of the isomeric mixture 8(S)-E-(5-hydroxy-3-methylpent-3-en-1-yn-yl)-2(R),3(R),7,7,9(R)-pentamethyl-1,4-dioxaspira[4.5]decan-8-ol and 8(R)-E-(5-hydroxy-3-methylpent-3-en-1-yn-yl-2(R),3(R),7,7,9(R)pentamethyl-1,4-dioxoaspira[4.5]decan-8-ol dissolved in 60 ml of pyridine, was treated with 3.7g of benzoylchloride at room temperature. The reaction mixture was stirred at room temperature for 17 hours then it was diluted with ether and the organic phase was washed twice with cooled 1N-sulfuric acid (+ice), once with brine, saturated sodium bicarbonate, brine and dried on magnesium sulfate. After removal of the solvents, remained 8.4g (ca 100%) of material that was chromatographed on 210 grams aluminum oxide, benzene-ether (9:1 parts by volume) eluted 5.31g of the 8(S)-E-(5-benzoyloxy-3-methylpent-3-en-1-yn-yl)-2(R),3(R),3(R),7,7,9(R)-pentamethyl-1,4-dioxaspira[4.5]decan-8-ol.

EXAMPLE 10

4.53g of 8(S)-E-(5-benzoyloxy-3-methylpent-3-en-1-yn-yl)-2(R),3(R),7,7,9(R)-pentamethyl-1,4-dioxaspira[4.5]decan-8-ol was treated with 40 ml of a 5% by weight potassium hydroxide in 95% aqueous methanolic solution. The mixture was refluxed for 30 minutes. Ca.

20 ml of methanol was evaporated in vacuo. The rest was diluted with ether and washed three time with brine. The organic phase was dried on magnesium sulfate and the solvent evaporated at reduced pressure to give of crude material 8(S)-E-(5-hydroxy-3-methylpent-3-en-1-yn-yl)-2(R),3(R),7,7,9(R)-pentamethyl-1,4-dioxaspiro[4.5]decan-8-ol(ca 100%). Crystallization from hexane-ether afforded 3.25g of material, sufficiently pure to be used for the next step (m.p.85°–87° C.). An analytical sample, obtained by repeated crystallization from hexane-ether, gave following data: m.p.86.5°–87.5° C.

EXAMPLE 11

1(S)-E-(5-Hydroxy-3-methyl-3-penten-1-ynyl)-2,2,6(R)-trimethylcyclohexan-4-on-1-ol 1g of compound 8(S)-E-(5-hydroxy-3-methylpent-3-en-1-yn-yl)-2(R),3(R),7,7,9(R)-pentamethyl-1,4-dioxaspiro[4.5]decan-8-ol in 30 ml of acetone was treated with 2 ml 1N-aqueous sulfuric acid and stirred at 50° C. for 24 hours. The acid was neutralized with 1N-aqueous sodium hydroxide. Then most of the acetone was removed in vacuo. The residue (ca. 10 ml of solution) was diluted with ether and the organic phase was washed twice with brine, dried on magnesium sulfate and evaporated in vacuo.

0.820g of 1(S)-E-(5-Hydroxy-3-methyl-3-penten-1-ynyl)-2,2,6(R)-trimethylcyclohexan-4-on-1-ol(ca. 90.5% by GC-analysis) was used for the next step.

EXAMPLE 12

1(S)-E-(5-Hydroxy-3-methyl-3-penten-1-ynyl)-2,2,6(R)-trimethyl-1,4(R)-cyclohexandiol To a suspension of 3 g of tri-tert-butoxy aluminum hydride in 15 ml of tetrahydrofuran was added 0.82 g of 1(S)-E-(5-hydroxy-3-methyl-3-penten-1-ynyl)-2,2,6(R)-trimethylcyclohexan-4-on-1-ol in 5 ml of tetrahydrofuran at room temperature and then the mixture was stirred overnight at the same temperature. The excess of reagent was destroyed with 5% aqueous acetic acid (pH ca 5). The flask was rinsed with ether and the ethereal extracts were washed twice with brine, dried on magnesium sulfate anhydrous and evaporated at reduced pressure to give 0.805g of crude material. Crystallization from ether afforded 0.545g (ca 70% of the theory) of pure 1(S)-E-(5-hydroxy-3-methyl-3-penten-1-ynyl)-2,2,6(R)-trimethyl-1,4(R)-cyclohexandiol, an analytical sample obtained by repeated crystallization from methanol-ether had the following melting point: m.p.: 128°–130.5° C.

EXAMPLE 13

4(R)-Acetoxy-1(S)-E-(5-acetoxy-3-methyl-3-penten-1-ynyl)-2,2,6(R)-trimethyl-1-cyclohexanol 50 mg of 1(S)-E-(5-hydroxy-3-methyl-3-penten-1-ynyl)-2,2,6(R)-trimethyl-1,4(R)-cyclohexandiol, dissolved in 1 ml of a mixture of acetic anhydride and pyridine (1:1 parts by volume) was stirred overnight at room temperature. The solvents were evaporated 62 mg of crude material was crystallized from ether-hexane to give 60 mg of pure 4(R)-acetoxy-1(S)-E-(5-acetoxy-3-methyl-3-penten-1-ynyl)-2,2,6(R)-trimethyl-1-cyclohexanol (m.p.: 86°–87° C.; $[\alpha]_D^{25} = -21.59$, 1% in dioxane; GC-analysis, 97% pure, NMR no isomers detected).

EXAMPLE 14

78 g of 4(R),6(R)-4-hydroxy-2,2,6-trimethyl-cyclohexanone dissolved in 170 ml of methylenechloride and containing 1 ml of a solution of 1% by weight p-toluenesulfonic acid in methanol was added to 100 ml of isopropenylmethylether at 5° to 10° C. (cold water bath) under argon. The reaction mixture was stirred at room temperature for 45 minutes. The solvents were carefully evaporated at reduced pressure (water bath not over 45° C.) to give 82.5 g (93.7%) of 4,4'(isopropylidenedioxy)-bis[(4R,6R)-2,2,6-trimethyl-cyclohexanone]

250 ml of tetrahydrofuran was added to a Grignard solution prepared as in Example 8 from 39 g of magnesium activated with iodine, 177 g of ethylbromide, 65 g of trans-pentol and 850ml tetrahydrofuran. The reaction mixture was stirred overnight at room temperature; then it was refluxed for 2 hours. After cooling, the reaction mixture was poured into 300ml of a 1N-aqueous sulfuric acid solution mixed with ice cubes. The ethereal solution was washed with brine, saturated aqueoussodium bicarbonate solution, brine, dried on magnesium sulfate and the solvent evaporated in vacuo.

167.2g of crude material was crystallized twice from methanol-ether to give 70.9 g of compound 1(S)-E-(5-hydroxy-3-methyl-3-penten-1-ynyl)-2,2,6(R)-trimethyl-1,4(R)-cyclohexandiol (m.p. 118°–124° C.).

EXAMPLE 15

E-5-[4(R)-Acetoxy-2,2,6-trimethyl-cyclohex-6-en-1-yl]-3-methyl-pent-2-en-4-yn-1-ol acetate 1.68 g of 4(R)-acetoxy-1(S)-E-(5-acetoxy-3-ethyl-3-penten-1-ynyl)-2,2,6(R)-trimethyl-1-cyclohexanol dissolved in 40 ml of pyridine was treated with 1.8 ml of phosphoroxychloride (d=1.67) at room temperature. The reaction mixture was then heated at 90° C. for 18 hours.

1.02 g of crude material was chromatographed on 50 grams of aluminum oxide, 0.623g of E-5-[4(R)-acetoxy-2,2,6-trimethyl-cyclohex-6-en-1-yl]-3-methyl-pent-2-en-4-yn-1-ol acetate was eluted with a mixture of benzene-hexane 9:1 parts by volume. This material was a light yellow oil.

I claim:

1. A compound of the formula

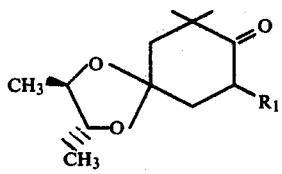

wherein R₁ is ━ CH₃ or lllCH₃.

2. The compound of claim 1 wherein said compound is 2(R),3(R),7,7,9(R)-pentamethyl-1,4-dioxaspiro-[4.5]-decan-8-one.

3. A compound wherein said compound is 8(S)-ethynyl-2-(R),3(R),7,7,9(R)-pentamethyl-1,4-dioxaspiro[4.5]decan-8-ol.

4. A composition selected from the group consisting of a compound of the formula

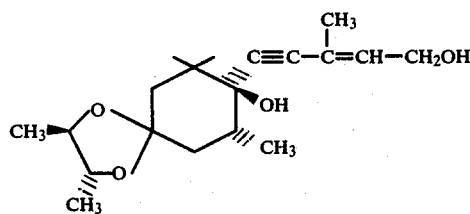

and mixtures thereof with a compound of the formula

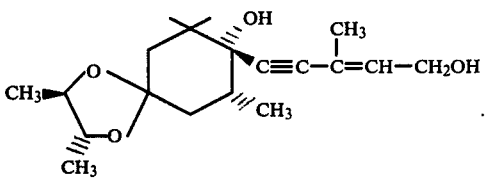

5. The compound of claim 4 wherein said compound is 8(S)-E-(5-hydroxy-3-methyl-3-penten-1-ynyl)-2(R),3(R),7,7,9-pentamethyl-1,4-dioxaspiro[4,5-]decan-8-ol.

6. The compound of claim 4 wherein said 8(S)-E-(5-hydroxy-3-methylpent-3-en-1-ynyl)-2(R),3(R),7,7,9(R)-pentamethyl-1,4-dioxaspiro[4.5]decan-8-ol is mixed with 8(R)-E-(5-hydroxy-3-methylpent-3-en-1-yn-yl)-2(R),3(R),7,7,9(R)pentamethyl-1,4-dioxaspiro[4,5]decan-8-ol.

7. A compound of the formula

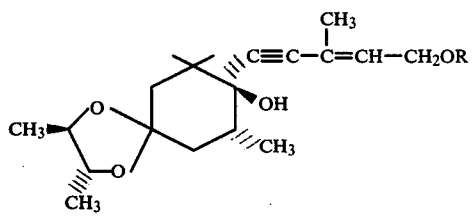

wherein R is benzoyl or lower alkanoyl.

8. The compound of claim 7 wherein said compound is 8(S)-E-(5-benzoyloxy-3-methylpent-3-en-1-yn-yl)-2(R),3(R),7,7,9(R)-pentamethyl-1,4-dioxaspiro[4.5]decan-8-ol.

* * * * *